United States Patent
Williams et al.

(10) Patent No.: US 10,542,992 B2
(45) Date of Patent: Jan. 28, 2020

(54) LOADING UNIT WITH STRETCHABLE BUSHING

(71) Applicant: Covidien LP, Mansfield, MA (US)

(72) Inventors: Justin Williams, Southbury, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 693 days.

(21) Appl. No.: 15/262,091

(22) Filed: Sep. 12, 2016

(65) Prior Publication Data
US 2017/0105737 A1    Apr. 20, 2017

Related U.S. Application Data

(60) Provisional application No. 62/243,167, filed on Oct. 19, 2015.

(51) Int. Cl.
*A61B 17/115* (2006.01)
*A61B 17/072* (2006.01)
*A61B 17/10* (2006.01)

(52) U.S. Cl.
CPC ........ *A61B 17/1155* (2013.01); *A61B 17/072* (2013.01); *A61B 17/07207* (2013.01); *A61B 17/105* (2013.01); *A61B 2017/07257* (2013.01); *A61B 2017/07271* (2013.01); *A61B 2017/1157* (2013.01)

(58) Field of Classification Search
CPC . A61B 17/1155; A61B 17/072; A61B 17/105; A61B 17/07207; A61B 2017/00473; A61B 2017/00477; A61B 2017/1157; A61B 2017/07257; A61B 2017/07271
USPC ........................................... 227/175.1–182.1
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Robert F Long

(57) ABSTRACT

A shell assembly includes a housing, a cartridge, and a hollow bushing. The housing defines a longitudinal axis and a cavity. The cartridge is supported on the housing and includes a plurality of staples. The hollow bushing is positioned within the cavity of the housing. The hollow bushing includes a distal portion and a proximal portion formed of a rigid material, and an expandable portion that connects the distal and proximal portions. The hollow bushing has an initial configuration where the hollow bushing defines a first length along the longitudinal axis and a stretched configuration where the hollow bushing defines a second length along the longitudinal axis which is greater than the first length.

17 Claims, 11 Drawing Sheets

(56) References Cited

U.S. PATENT DOCUMENTS

| | | |
|---|---|---|
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,240,163 A * | 8/1993 | Stein ............... A61B 17/072 227/175.3 |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,389,098 A * | 2/1995 | Tsuruta ............ A61B 17/00234 606/41 |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,452,836 A * | 9/1995 | Huitema ............ A61B 17/072 227/176.1 |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,544 A * | 9/1997 | Schulze ........... A61B 17/07207 227/176.1 |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,871 A * | 3/1998 | Clark ................ A61B 17/072 227/175.1 |
| 5,732,872 A | 3/1998 | Bolduc et al. |
| 5,749,896 A | 5/1998 | Cook |
| 5,758,814 A | 6/1998 | Gallagher et al. |
| 5,779,130 A * | 7/1998 | Alesi ............... A61B 17/07207 227/176.1 |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,954,259 A * | 9/1999 | Viola ............... A61B 17/07207 227/176.1 |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |

(56) References Cited

U.S. PATENT DOCUMENTS

| | | |
|---|---|---|
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,617,961 B2 * | 11/2009 | Viola ............... A61B 17/07207 227/175.1 |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |

(56) References Cited

U.S. PATENT DOCUMENTS

| | | |
|---|---|---|
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,789,737 B2 | 7/2014 | Hodgkinson et al. |
| 9,016,547 B2 * | 4/2015 | Mozdzierz ......... A61B 17/1155 227/179.1 |
| 9,173,658 B2 * | 11/2015 | Nolan ................. A61B 17/1114 |
| 9,204,879 B2 * | 12/2015 | Shelton, IV ...... A61B 17/07207 |
| 10,406,666 B2 * | 9/2019 | Lai ........................ B25C 5/1617 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2005/0113821 A1 * | 5/2005 | Pendekanti .......... A61B 17/072 606/41 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0078486 A1 * | 4/2007 | Milliman ............ A61B 17/1114 606/219 |
| 2009/0090764 A1 * | 4/2009 | Viola ............... A61B 17/07207 227/176.1 |
| 2009/0212088 A1 * | 8/2009 | Okada ................ A61B 17/1114 227/175.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |

(56) References Cited

U.S. PATENT DOCUMENTS

| | | |
|---|---|---|
| 2010/0320252 A1* | 12/2010 | Viola .............. A61B 17/07207 227/176.1 |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0061447 A1* | 3/2012 | Williams .............. A61B 17/115 227/175.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0234890 A1 | 9/2012 | Aronhalt et al. |
| 2012/0253329 A1 | 10/2012 | Zemlok et al. |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0334279 A1* | 12/2013 | Prior .................... A61B 17/115 227/175.1 |
| 2014/0008413 A1 | 1/2014 | Williams |
| 2014/0012317 A1 | 1/2014 | Orban et al. |
| 2014/0042206 A1 | 2/2014 | Milliman |
| 2014/0151429 A1 | 6/2014 | Scheib et al. |
| 2014/0151430 A1* | 6/2014 | Scheib .............. A61B 17/1155 227/175.1 |
| 2014/0263556 A1* | 9/2014 | Mozdzierz ......... A61B 17/1155 227/176.1 |
| 2015/0351769 A1* | 12/2015 | Lee .................... A61B 17/1155 227/179.1 |
| 2016/0106406 A1 | 4/2016 | Cabrera et al. |
| 2017/0281169 A1* | 10/2017 | Harris ................ A61B 17/1155 |
| 2017/0281181 A1* | 10/2017 | Matonick ......... A61B 17/07292 |
| 2017/0281182 A1* | 10/2017 | Nativ ................ A61B 17/0644 |
| 2017/0281189 A1* | 10/2017 | Nalagatla ........... A61B 17/0644 |
| 2018/0078260 A1* | 3/2018 | Matonick ............ A61B 17/072 |
| 2018/0206846 A1* | 7/2018 | Guerrera ............ A61B 17/1155 |
| 2018/0317916 A1* | 11/2018 | Wixey ............. A61B 17/07207 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2676617 A1 | 12/2013 |
| EP | 2873380 A1 | 5/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |

OTHER PUBLICATIONS

European Examination Report from Appl. No. 14181908.6 dated May 3, 2016.

Extended European Search Report dated Dec. 13, 2016, issued in EP Application No. 16194285.

* cited by examiner

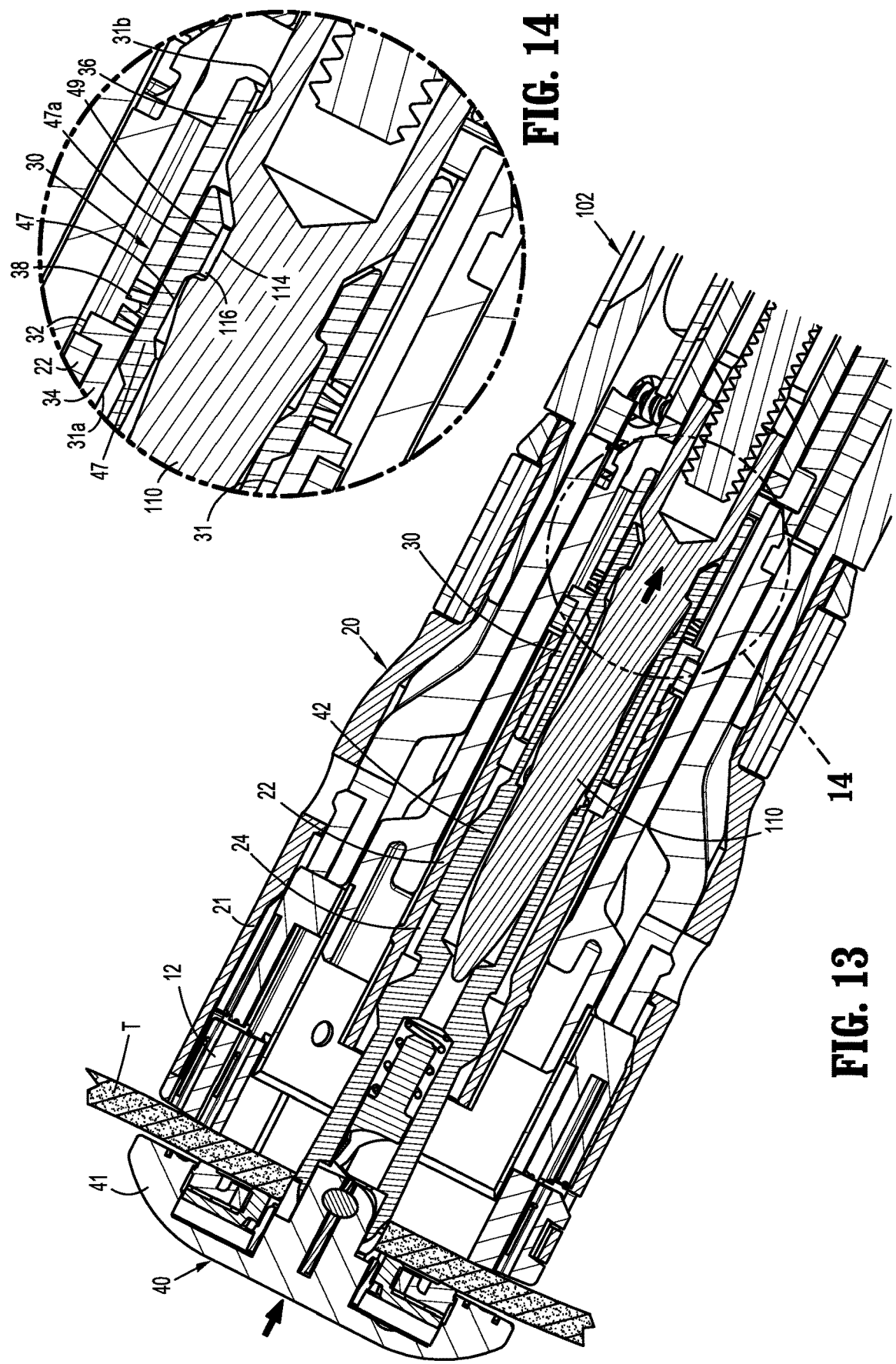

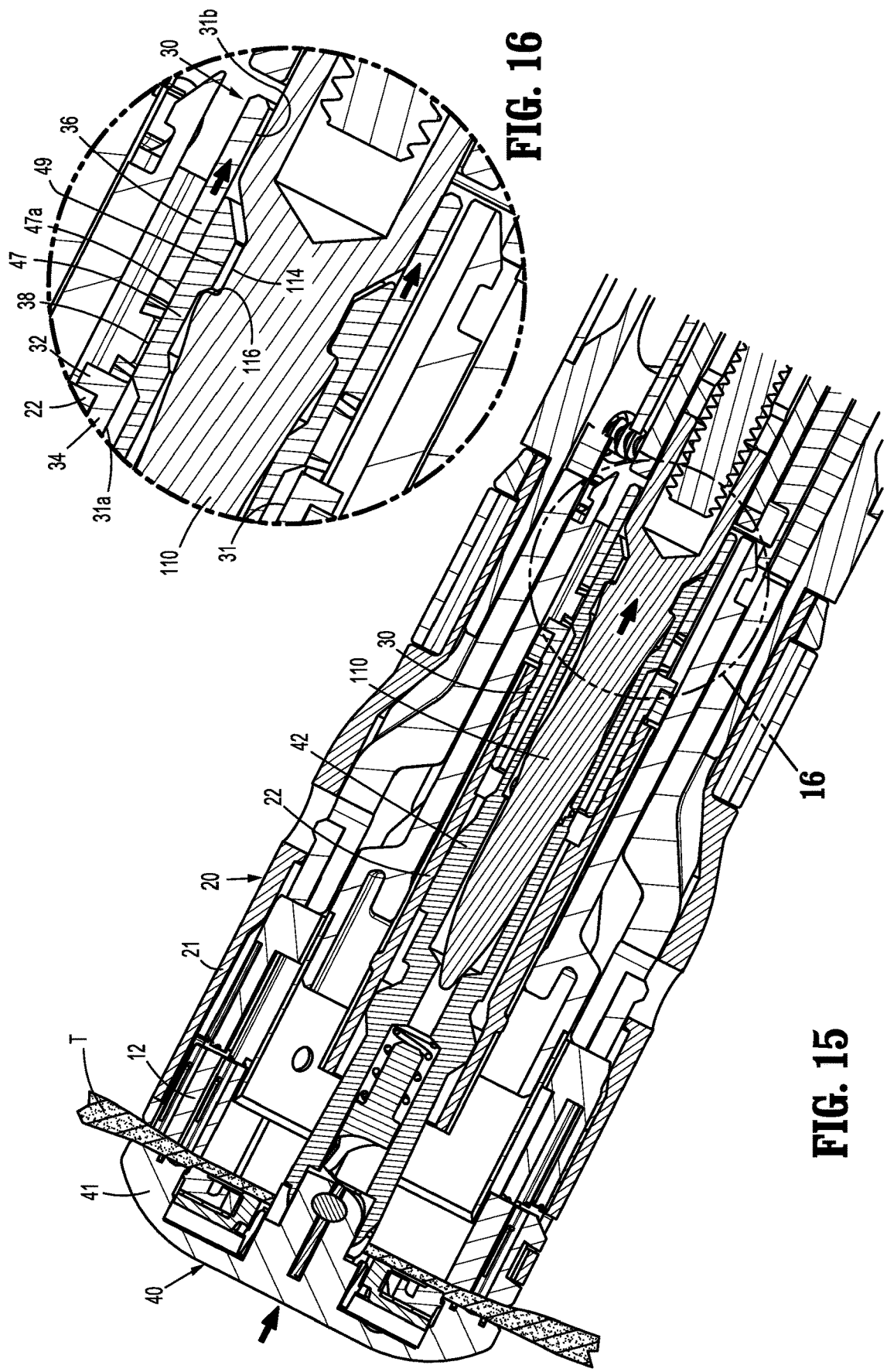

LOADING UNIT WITH STRETCHABLE BUSHING

CROSS-REFERENCE TO RELATED APPLICATIONS

This application claims the benefit of and priority to U.S. Provisional Patent Application No. 62/243,167 filed Oct. 19, 2015, the entire disclosure of which is incorporated by reference herein.

BACKGROUND

1. Technical Field

The present disclosure relates generally to surgical stapling instruments. More specifically, the present disclosure relates to circular surgical stapling instruments with stretchable bushings.

2. Background of Related Art

Surgical stapling instruments configured to join tissue during a surgical procedure are well known. These devices include linear end effectors which are oriented either parallel or transverse to a longitudinal axis of the instrument. Typically, circular stapling instruments include a cartridge or shell assembly that is fixedly attached to a distal end of the instrument and a detachable anvil moveably supported in relation to the shell assembly. Circular stapling instruments also include an anvil retainer that extends through the shell assembly and is coupled to the anvil to facilitate movement of the anvil towards the shell assembly and to clamp tissue between the shell assembly and the anvil. As the anvil is approximated in relation to the shell assembly, the coupling between the anvil and the anvil retainer may disengage in response to tension on the anvil. Typically, a bushing is provided to prevent disengagement of the coupling between the anvil and the anvil retainer. As the bushing is engaged, frictional forces between the bushing and the anvil retainer and/or the anvil increases such that the force required to approximate the anvil towards the shell assembly is increased.

A need exists for a coupling mechanism for a circular stapling instrument that reduces the frictional forces required to prevent disengagement of the coupling between the anvil and the anvil retainer.

SUMMARY

In an aspect of the present disclosure, a shell assembly includes a housing, a cartridge, and a hollow bushing. The housing defines a longitudinal axis and a cavity. The cartridge is supported on the housing and includes a plurality of staples. The hollow bushing is positioned within the cavity and includes a distal portion and a proximal portion that are formed of a rigid material. The hollow bushing also includes an expandable portion that connects the distal and proximal portions. The hollow bushing has an initial configuration wherein the hollow bushing defines a first length along the longitudinal axis and a stretched configuration wherein the hollow bushing defines a second length along the longitudinal axis that is greater than the first length.

In aspects, the expandable portion includes a plurality of legs that are bent in the initial configuration and are straightened in the stretched configuration. In the stretched configuration, each leg of the plurality of legs may be aligned with the longitudinal axis. Additionally or alternatively, the expandable portion may define a helical slot that passes through the expandable portion. The helical slot may be compressed in the initial configuration and expanded in the stretched configuration.

In some aspects, the shell assembly includes an inner cylinder that is positioned within the cavity. The hollow bushing may be secured to the inner cylinder. The hollow bushing may include a central flange that is positioned between the distal portion and the expandable portion and sized to prevent the hollow bushing from moving distally through the inner cylinder. The distal portion of the hollow bushing may include engagement features that longitudinally fix the hollow bushing within the housing. The engagement features may include annular ribs that engage the inner cylinder.

In another aspect of the present disclosure, a surgical instrument includes an anvil retainer, an anvil assembly, and a shell assembly. The anvil retainer has distal and proximal end portions. The anvil assembly includes an anvil head and an anvil shaft that extends proximally from the anvil head. The anvil shaft has resilient legs that are secured about the anvil retainer. The shell assembly includes a housing, a cartridge, and a hollow bushing. The housing defines a longitudinal axis and a cavity. The cartridge is supported on the housing and includes a plurality of staples. The hollow bushing is positioned within the cavity and is configured to prevent the anvil shaft from being disengaged from the anvil retainer. The hollow bushing includes a distal portion and a proximal portion that are formed of a rigid material and an expandable portion that connects the distal and proximal portions together. The hollow bushing has an initial configuration wherein the hollow bushing defines a first length along the longitudinal axis and a stretched configuration wherein the hollow bushing defines a second length along the longitudinal axis that is greater than the first length.

In aspects, the proximal end portion of the anvil retainer defines a notch and the resilient legs of the anvil shaft include a retaining ring that extends inward from an inner surface of the anvil shaft such that the retaining ring is positionable within the notch of the anvil retainer to secure the anvil shaft to the anvil retainer. The resilient legs of the anvil shaft may define an expandable collar that radially expands in response to retraction of the anvil retainer. The hollow bushing may be positioned to prevent the retaining ring from being disengaged from the notch of the anvil retainer when the resilient legs of the anvil shaft are disposed within the hollow bushing. The retraction of the anvil retainer may approximate the anvil head towards the shell assembly.

In some aspects, the resilient legs of the anvil shaft engage the proximal portion of the hollow bushing to expand the hollow bushing from the initial configuration towards the stretched configuration in response to retraction of the anvil retainer. The distal end portion of the anvil retainer may be tapered and the resilient legs of the anvil shaft may radially expand as the anvil shaft receives the tapered distal end portion of the anvil retainer. The anvil retainer may be extendable distally such that a notch defined by the anvil retainer is positionable beyond the hollow bushing to couple the anvil retainer to the anvil shaft.

In certain aspects, the proximal portion of the hollow bushing includes an engagement flange that extends inward from an inner surface of the hollow bushing. The expandable collar may be configured to engage the engagement flange. The engagement flange of the expandable collar with the engagement flange may expand the hollow bushing from the initial configuration towards the stretched configuration in response to retraction of the anvil retainer. The expandable collar may be configured to radially expand such that an outer surface of the expandable collar engages an inner surface of the hollow bushing. The outer surface of the expandable collar may frictionally engage the inner surface of the hollow bushing to expand the hollow bushing from the initial configuration towards the stretched configuration.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 13 is a cross-sectional view of the loading unit of FIG. 12 with the anvil approximated towards the shell assembly to clamp the tissue between the anvil and the shell assembly with the bushing in the initial configuration;

FIG. 14 is an enlarged view of the indicated area of detail of FIG. 13;

FIG. 15 is a cross-sectional view of the loading unit of FIG. 13 with the anvil further approximated towards the shell assembly and the bushing in the stretched configuration;

FIG. 16 is an enlarged view of the indicated area of detail of FIG. 15; and

DETAILED DESCRIPTION OF EMBODIMENTS

Figure 1A:
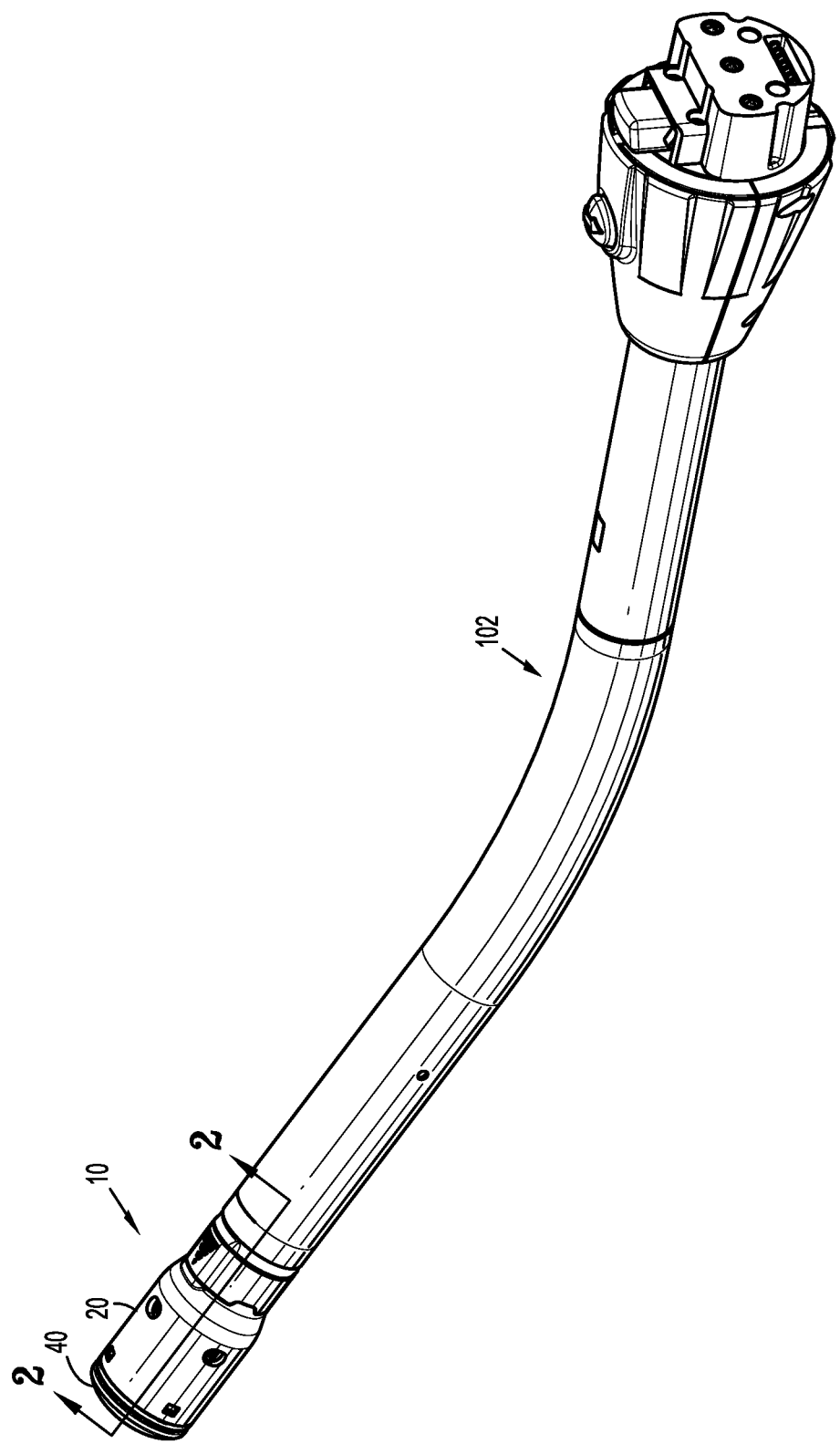
FIG. 1A is a perspective view of a circular stapler adapter with a loading unit in accordance with the present disclosure disposed at a distal end of the adapter.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a stretchable bushing of a shell assembly of a circular stapling instrument or loading unit. The bushing prevents a proximal end of an anvil shaft of an anvil assembly from becoming disengaged from an anvil retainer of the stapling instrument during approximation of the anvil assembly and the shell assembly while reducing a retraction force required to approximate the anvil assembly and the shell assembly. Specifically, the bushing stretches from an initial configuration to a stretched configuration when engaged by a proximal end of the anvil shaft. The bushing reduces the retraction force by stretching instead of requiring the retraction force to overcome frictional forces between the anvil shaft and the bushing. The anvil shaft may frictionally engage the bushing or may engage a flange of the bushing to stretch the bushing.

Figure 1B:
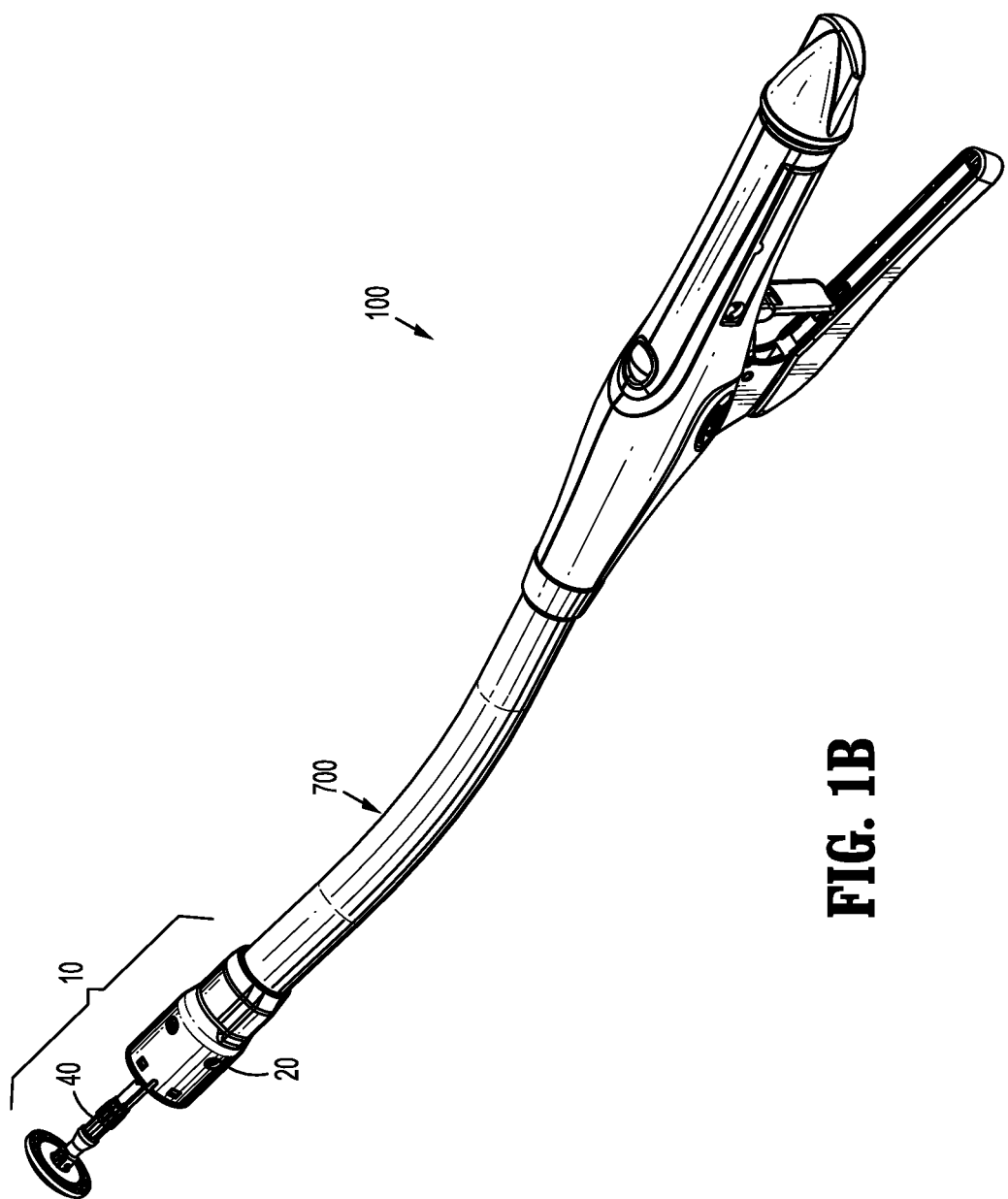
FIG. 1B is a perspective view of a surgical stapling circular instrument with the loading unit of FIG. 1A disposed at a distal end of the surgical instrument.

With reference to FIGS. 1A and 1B, a loading unit 10 is provided in accordance with an embodiment of the present disclosure. The loading unit 10 is configured for selective connection to a powered hand held electromechanical instrument (not shown) via an adapter 102 (FIG. 1A) of a surgical instrument. Alternatively, the loading unit 10 can be configured for connection directly to a manually actuated handle assembly or stapling instrument 100 (FIG. 1B) such as described in U.S. Pat. No. 8,789,737 ("the '737 Patent"), which is incorporated herein in its entirety by reference.

For a detailed description of the structure and function of an exemplary adapter and loading unit, please refer to commonly owned U.S. Provisional Patent Application Ser. No. 62/066,518, filed Oct. 21, 2014, entitled "Adapter, Extension, and Connector Assemblies for Surgical Devices." For a detailed description of the structure and function of an exemplary electromechanical instrument, please refer to commonly owned U.S. Patent Publication No. 2012/0253329, filed on May 31, 2012. Each of these applications is incorporated herein by reference in its entirety.

Figure 2:
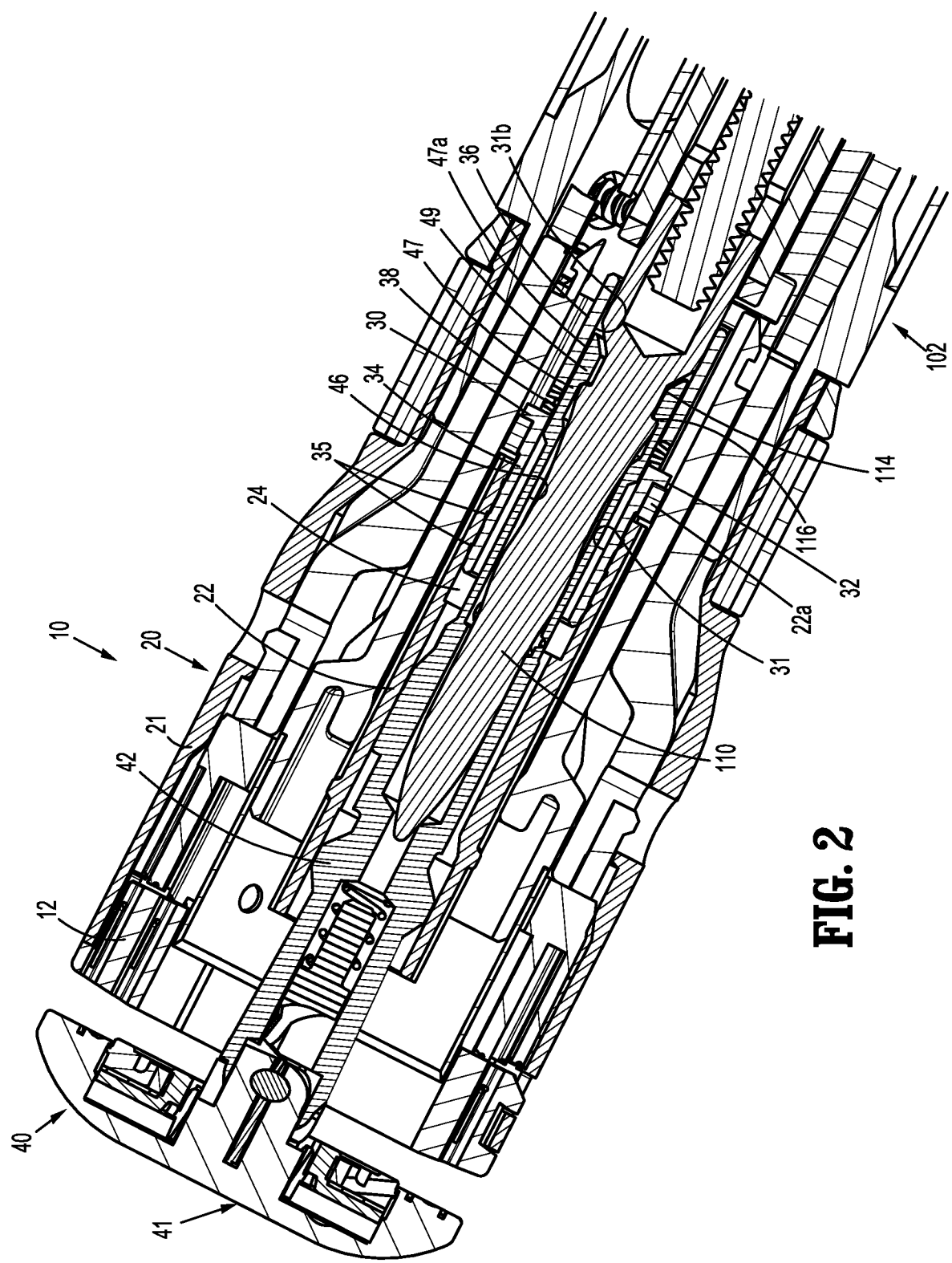
FIG. 2 is an enlarged cross-sectional view taken along the section line 2-2 of FIG. 1A.
Figure 3:
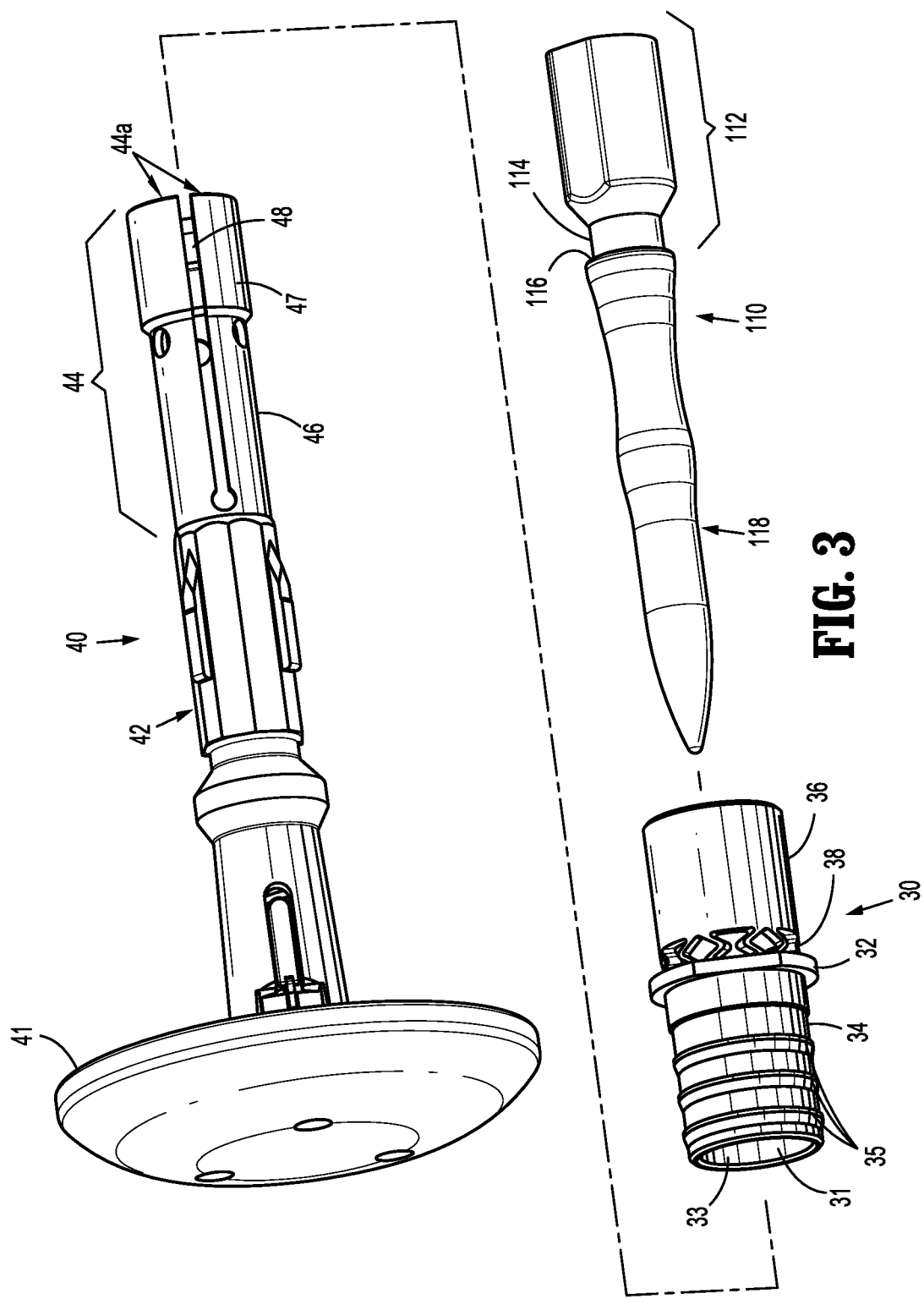
FIG. 3 is exploded perspective view of an anvil assembly and a bushing of the loading unit of FIG. 1A and a trocar of the circular stapler adapter of FIG. 1A.

Referring also to FIGS. 2 and 3, the loading unit 10 includes a shell assembly 20 and an anvil assembly 40. The shell assembly 20 may be releasably coupled or fixedly secured to the adapter 102 and includes a housing 21 supporting a staple cartridge 12. The housing 21 defines a cavity or central passage 24 and includes an inner cylinder 22 positioned within the central passage 24. In addition, the shell assembly 20 also includes a hollow bushing 30 that is positioned within the central passage 24 and longitudinally fixed to the inner cylinder 22 of the shell assembly 20. The anvil assembly 40 includes an anvil head 41 and an anvil shaft 42 that extends proximally from the anvil head 41. When the anvil shaft 42 is attached to the adapter 102, or the stapling instrument 100, the anvil shaft 42 is positioned at least partially within the inner cylinder 22 of the shell assembly 20 and extends into the bushing 30. The adapter 102, or the stapling instrument 100, includes an anvil retainer, e.g., trocar 110, that is received within the anvil shaft 42 when the anvil assembly 40 is connected to the trocar 110. The trocar 110 forms the distal end of an approximation assembly (not shown) and is movable to approximate the anvil head 41 and the staple cartridge 12 as described in detail below.

The anvil shaft 42 includes a proximal portion 44 including resilient legs 44a that define an annular recess 46 and one or more longitudinal slots 48. The proximal portion 44 of the legs 44a together define an expandable collar 47 that partially defines the annular recess 46. The longitudinal slots 48 allow the resilient legs 44a of the anvil shaft 42 to expand outwards as the trocar 42 is received within the anvil shaft 42. An inner surface of the anvil shaft 42 includes a retaining ring 49 (FIG. 6) that longitudinally secures the anvil shaft 42 to the trocar 110 as detailed below.

Figure 6:
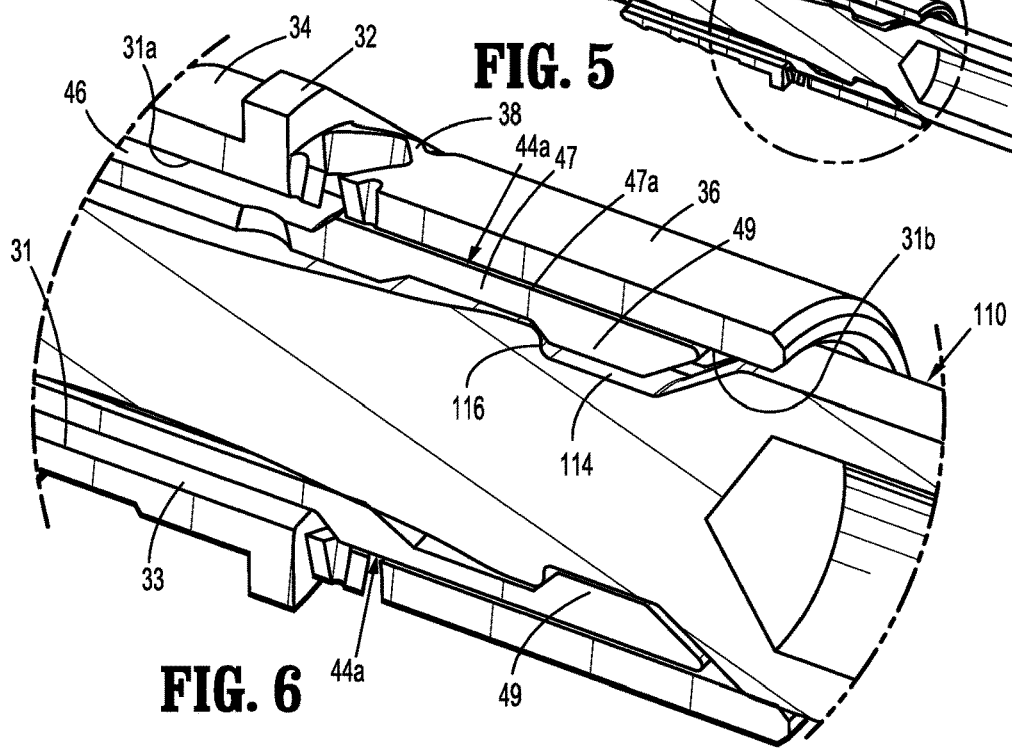
FIG. 6 is an enlarged view of the indicated area of detail of FIG. 5.

The trocar 110 includes a proximal end portion 112 and a tapered distal end 118. The proximal end portion 112 of the trocar 110 is secured to an approximation assembly (not shown) of the adapter 102 (FIG. 1A), or stapling instrument 100 (FIG. 1B), such as described in the '737 Patent. The proximal end portion 112 also defines a notch 114 that receives the retaining ring 49 of the anvil shaft 42 as shown in FIG. 6. The notch 114 is defined by a distal wall 116 that engages the retaining ring 49 of the anvil shaft 42 to draw or retract the anvil assembly 40 towards the shell assembly 20 as the trocar 110 is retracted within the adapter 102, or surgical instrument 100.

The bushing 30 is hollow and includes an inner surface 31, a central flange 32, a distal portion 34, and a proximal portion 36. The inner surface 31 defines a bushing passage 33 about a longitudinal axis of the shell assembly 20 that is in communication with the central passage 24 of the inner cylinder 22. The central flange 32 engages a distal end 22a (FIG. 2) of the inner cylinder 22 (FIG. 2) of the shell assembly 20 to prevent the bushing 30 from passing distally through inner cylinder 22. The distal portion 34 distally extends from the central flange 32 into the central passage 24 of the inner cylinder 22. The outer surface of the distal portion 34 includes engagement features 35 that engage the inner cylinder 22 (FIG. 2) of the shell assembly 20 to longitudinally fix the bushing 30 relative to the shell assembly 20. The engagement features 35 are shown as external annular ribs that engage the inner cylinder 22; however, it is contemplated that the engagement features 35 may be threads or another known engagement feature for fixing the bushing 30 to the inner cylinder 22 of the shell assembly 20. In addition, the outer surface of the distal portion 34 may be secured within the inner cylinder 22 of the shell assembly 20 using other known fastening techniques including adhesives, welding, or the like. The proximal portion 36 extends proximally from the central flange 32 and is connected to the central flange 32 by a stretchable or expandable section 38.

Portions of the shell assembly 20 may be constructed of a substantially rigid plastic material. In addition, the bushing 30, the anvil head 41, the anvil shaft 42, and the trocar 110 may be constructed of a metal or metal alloy, e.g., medical grade stainless steel.

Figure 4:
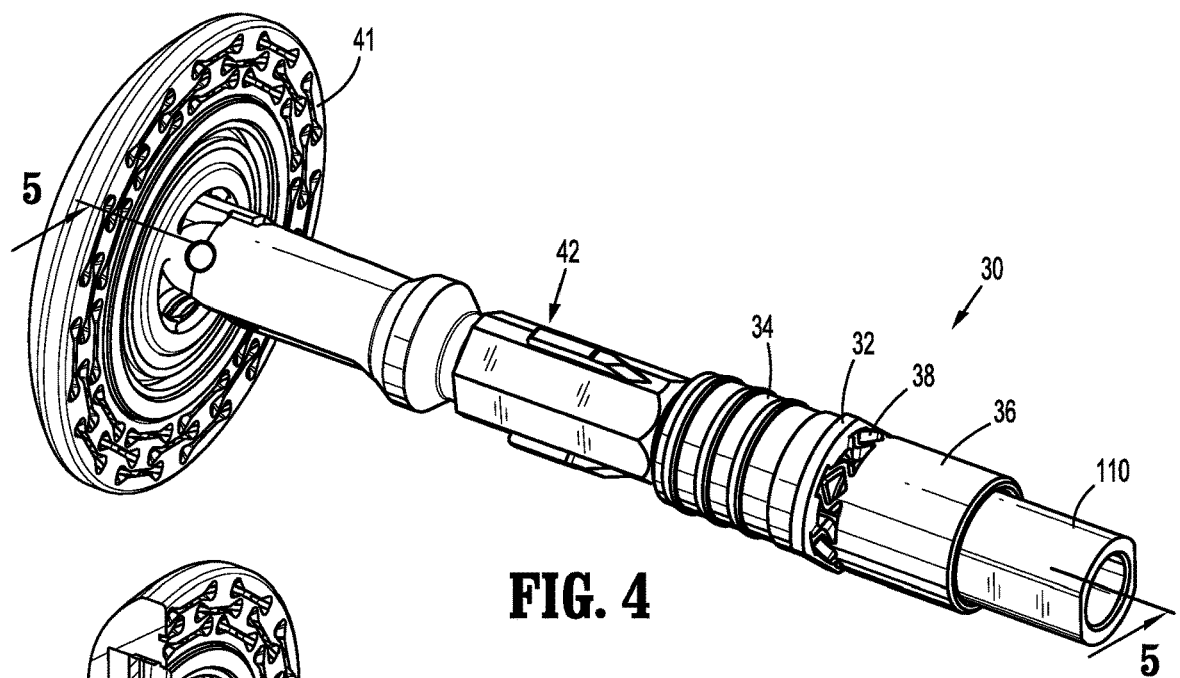
FIG. 4 is a perspective view of the assembled anvil assembly, bushing, and trocar of FIG. 3.
Figure 5:
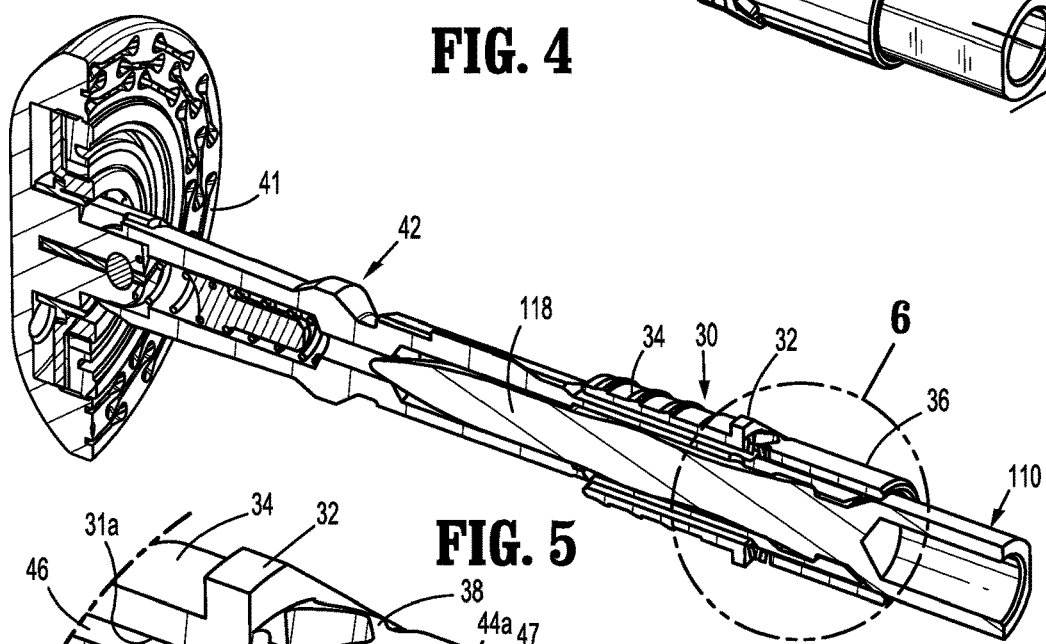
FIG. 5 is a cross-sectional view taken along the section line 5-5 of FIG. 4.

With reference to FIGS. 4-6, the trocar 110 is received within the annular recess 46 of the anvil shaft 42 to couple the anvil shaft 42 of the anvil assembly to the trocar 110. When the trocar 110 is coupled to the anvil assembly 40, the trocar 110 passes through the bushing 30 until the tapered distal end 118 of the trocar 110 is positioned within the retaining ring 49 of the anvil shaft 42 of the anvil assembly 40 and the anvil shaft 42 is received within the notch 114 of the trocar 110. As the trocar 110 passes through the recess 46 of the anvil shaft 42, the retaining ring 49 slides over the outer surface of the trocar 110 to effect radial expansion of the resilient legs 44a defining the collar 47 of the anvil shaft 42 as the diameter of the trocar 110 increases. It will be appreciated that the longitudinal slots 48 increase in width as the resilient legs 44a defining the expandable collar 47 radially expand. When the retaining ring 49 is longitudinally aligned with the notch 114, resilience of the resilient legs 44a of the anvil shaft 42 causes the retaining ring 49 to snap into the notch 114 as shown in FIG. 6. When the retaining ring 49 snaps into the notch 114, the retaining ring 49 may produce audible indicia, e.g., a click, to indicate that the anvil assembly 40 is secured to the trocar 110.

When the retaining ring 49 of the anvil shaft 42 is positioned within the notch 114 of the trocar 110 such that the anvil assembly is secured to the trocar 110, the trocar 110 can be retracted to draw the anvil shaft 42 through the bushing 30, and thus to approximate the anvil head 41 towards the staple cartridge 12 (FIG. 2). As anvil shaft 42 passes through the bushing 30, an outer surface 47a of the expandable collar 47 slides against the inner surface 31 of the bushing 30. It will be appreciated that the bushing 30 prevents the anvil shaft 42 from becoming disengaged from the trocar 110 by limiting the expansion of the resilient legs 44a defining the expandable collar 47 such that the retaining ring 49 remains disposed within the notch 114 of the trocar 110. As the retraction force is increased to draw the anvil shaft 42 though the bushing 30, the distal wall 116 defining the notch 114 of the trocar 110 engages the retaining ring 49 of the expandable collar 47 and cams the outer surface 47a of the expandable collar 47 outward towards the inner surface 31 of the bushing 30. This movement of the outer surface 47a of the anvil shaft 42 towards the inner surface 31 of the bushing 30 increases frictional forces between the outer surface 47a of the anvil shaft 42 and the inner surface 31 of the bushing 30. As such, the retraction force required to approximate the anvil assembly 40 and the shell assembly 20 are also increased.

When the anvil head 41 and the shell assembly 20 are substantially approximated as shown in FIG. 2, the expandable collar 47 is positioned at least partially within the proximal portion 36 of the bushing 30 such that the outer surface 47a of the stretchable collar 47 engages a proximal portion 31b of the inner surface 31 of the bushing 30 proximal to the expandable section 38 of the bushing 30. When the retraction force is applied by the trocar 110 to retract the anvil shaft 42 and, thus, the anvil assembly 40 proximally, the outer surface 47a of the expandable collar 47 of engages the proximal portion 31b of the inner surface 31 of the bushing 30 to deform the stretchable section 38 such that the proximal portion 36 of the bushing 30 is moved proximally away from the central flange 32 of the bushing 30. Since the force required to deform the expandable section 38 is less than the frictional forces between the inner surface 31 of the bushing 30 and the outer surface 47a of the expandable collar 47, the retraction force required to fully approximate the anvil head 41 and the shell assembly 20, as shown in FIG. 2, is lessened or reduced.

It is contemplated that the proximal portion 31b of the inner surface 31 of the bushing 30 may have a higher friction surface than the distal portion 31a of the inner surface 31 such that the outer surface 47a of the expandable collar 47 substantially slides across the distal portion 31a and frictionally engages the proximal portion 31b of the inner surface 31. Additionally or alternatively, the proximal portion 31b may have a diameter slightly smaller than the distal portion 31a such that the expandable collar 47 engages the proximal portion 31b before engaging the distal portion 31a.

Figure 7:
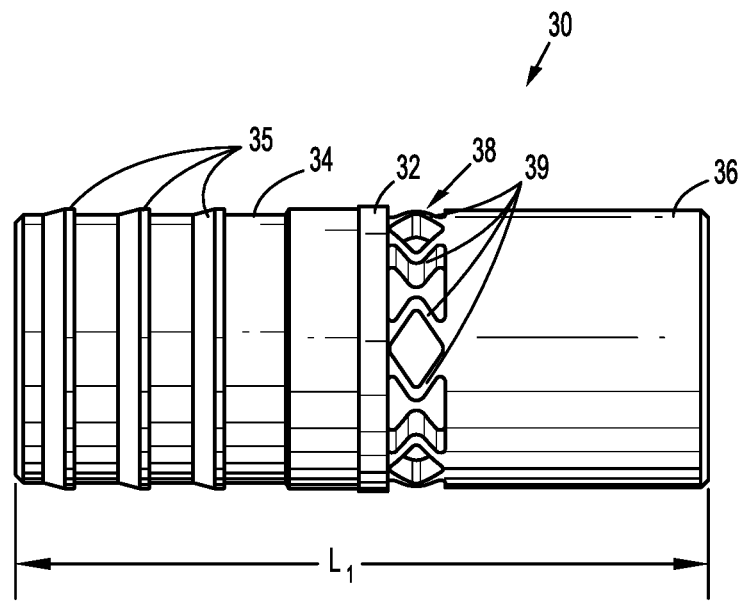
FIG. 7 is a side view of a bushing of FIG. 3 in an initial configuration.
Figure 8:
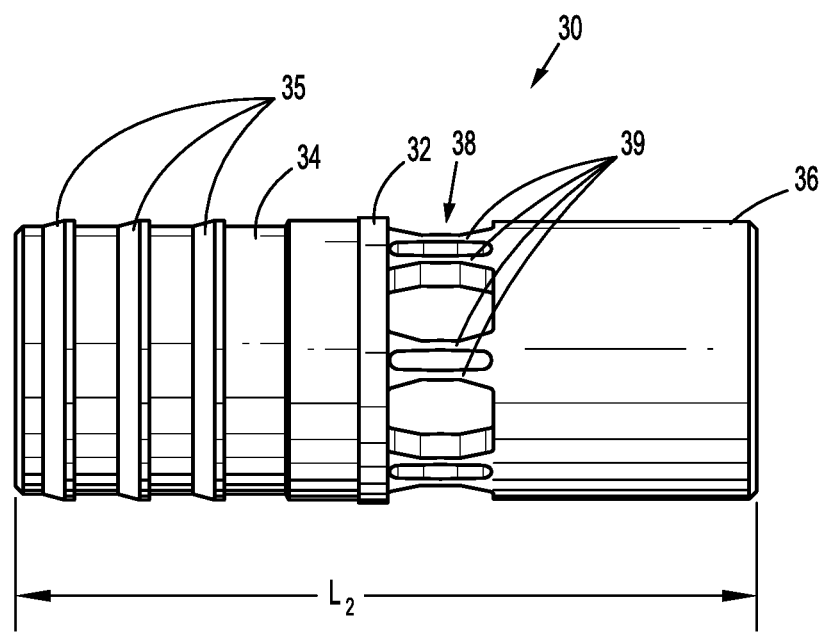
FIG. 8 is a side view of the bushing of FIG. 7 in a stretched configuration.

Referring to FIGS. 7 and 8, the expandable section 38 of the bushing 30 allows the bushing 30 to transition between an initial configuration (FIG. 7) and a stretched configuration (FIG. 8). In embodiments, the expandable section 38 is formed by legs 39 that connect the central flange 32 to the proximal portion 36. In the initial configuration, the legs 39 are bent such that the bushing 30 has a first length $L_1$ as shown in FIG. 7. In the stretched configuration, the legs 39 are substantially straight, such that the bushing 30 has a second length $L_2$ that is greater than the first length $L_1$. In the stretched configuration, the legs 39 are substantially aligned with the longitudinal axis of the shell assembly. The thickness and geometry of the legs 39 may be varied to calibrate the retraction force required to straighten the legs 39. It is contemplated that the legs 39 may be resilient such that the legs 39 return to the initial configuration when the trocar 110 is moved distally or the anvil shaft 42 moves proximally. For example, upon unclamping of tissue from between the anvil head 41 and the shell assembly 20, the resilient legs 44a of the anvil shaft 42 are no longer gammed outwardly and the friction forces between the collar 47 and the inner surface 31 of the bushing 30 are greatly reduced.

Figure 9:
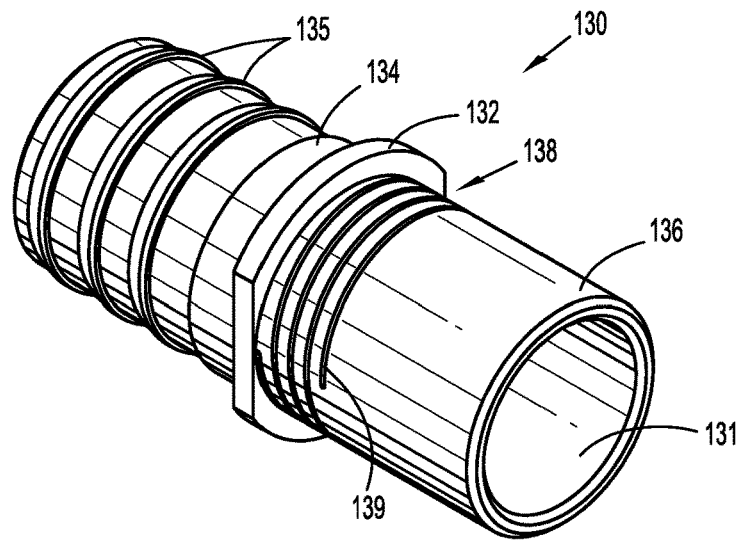
FIG. 9 is a perspective view of another bushing provided in accordance with the present disclosure.
Figure 10:
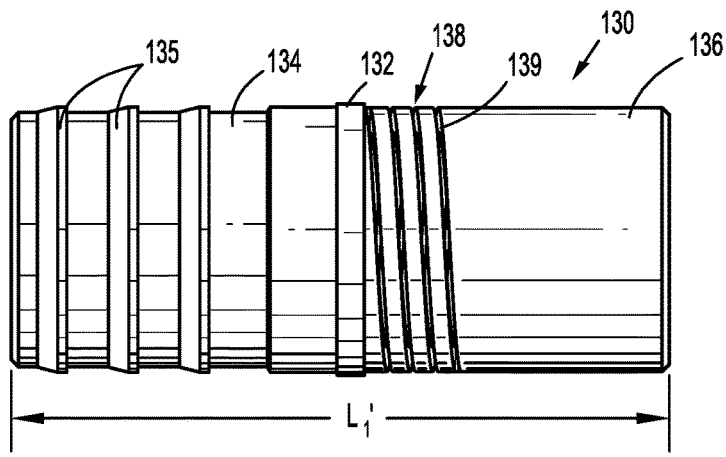
FIG. 10 is a side view of an bushing of FIG. 9 in an initial configuration.
Figure 11:
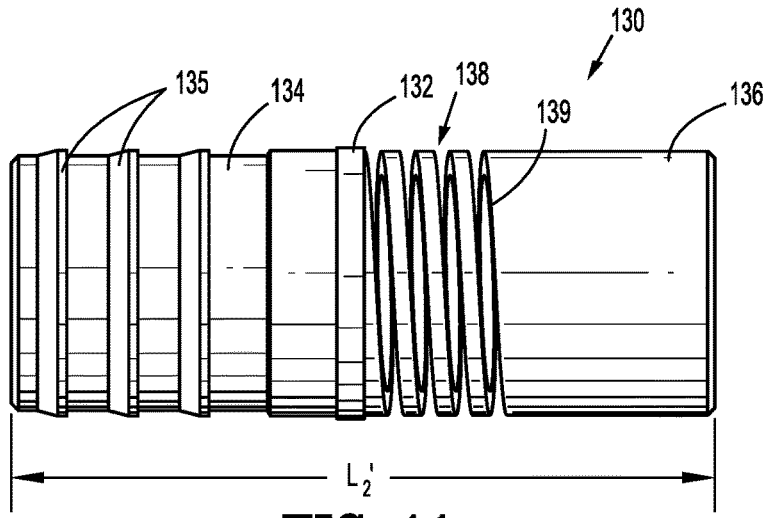
FIG. 11 is a side view of the bushing of FIG. 10 in a stretched configuration.

Referring to FIGS. 9-11, another hollow bushing 130 is provided in accordance with the present disclosure. The bushing 130 is similar to the bushing 30 detailed above with similar structures represented with reference numerals including a "1" preceding the previous reference numeral. The bushing 130 includes an expandable portion 138 between a central flange 132 and a proximal ring 136. The expandable portion 138 includes a helical slot 139 defined through the expandable portion 138. In an initial configuration of the bushing 130 (FIG. 10), the helical slot 139 is substantially compressed such that the bushing 130 has a first length $L_1'$. In a stretched configuration of the bushing 130 (FIG. 11), the helical slot 139 is expanded such that the bushing 130 has a second length $L_2'$ that is greater than the first length $L_1'$.

Figure 12:
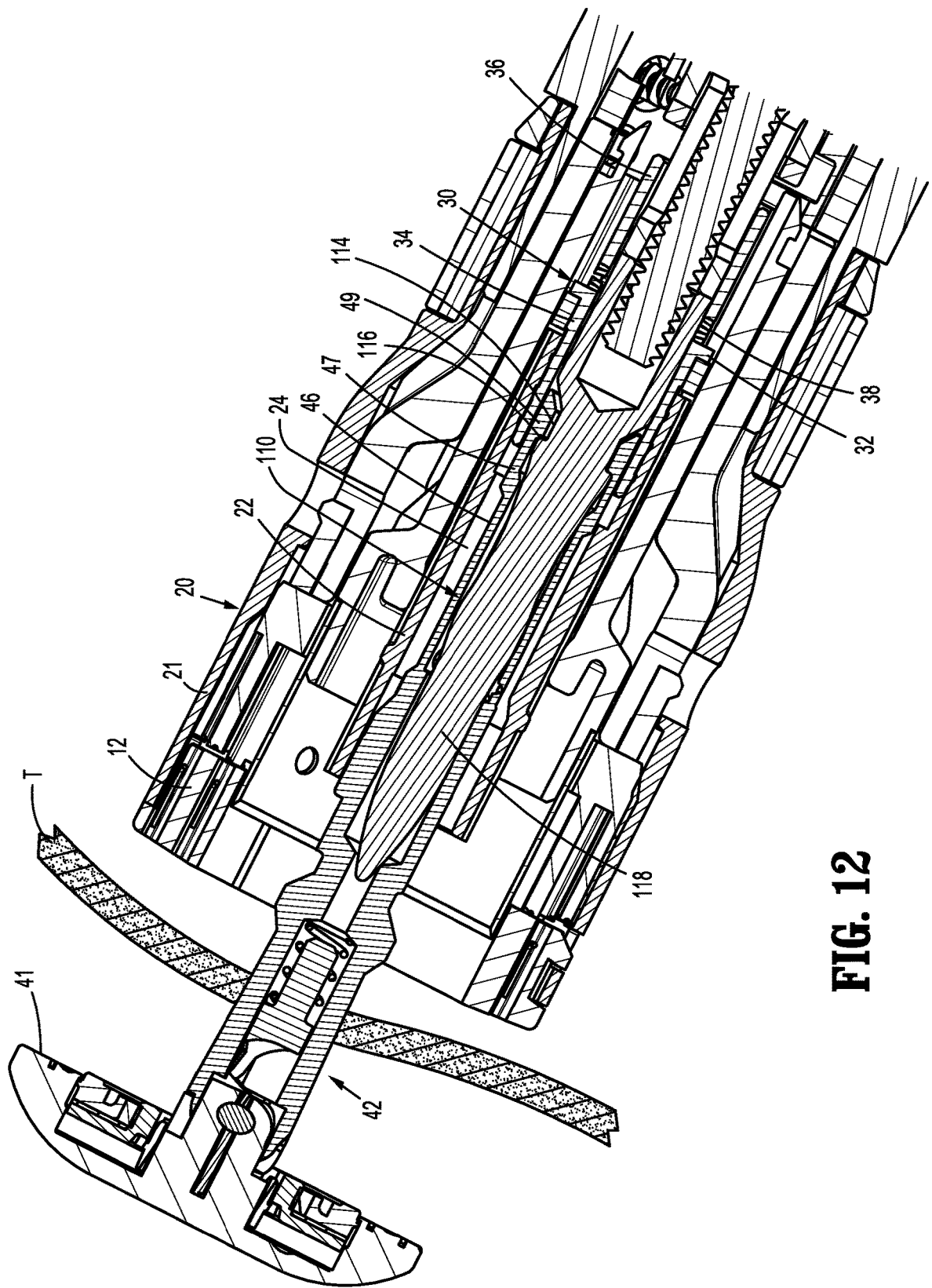
FIG. 12 is a cross-sectional view of the loading unit of FIG. 1A with the anvil spaced apart from the shell assembly and tissue positioned between the anvil and the shell assembly.

With reference to FIGS. 12-16, a method of clamping tissue in the loading unit 10 is described in accordance with the present disclosure. Initially, the trocar 110 is extended distally such that the tapered distal end 118 of the trocar 110 passes through the proximal portion 44 of the anvil shaft 42 until the retaining ring 49 of the expandable ring 47 is received within the notch 114 defined in the trocar 110 to secure the anvil shaft 42 to the trocar 110. As shown in FIG. 12, with the anvil assembly 40 secured to the trocar 110, the anvil shaft 42 is partially approximated such that the anvil assembly 42 is received within the bushing 30. With the anvil shaft 42 partially approximated, the anvil assembly 40 is positioned on one side of tissue T with the anvil shaft 42 passing through the tissue T. The tissue T may be a tubular organ, e.g., bowels. The shell assembly 20 is attached to the distal end of the adapter 102 (FIG. 1A), or a surgical instrument 100 (FIG. 1B), and is positioned on the opposite side of the tissue T. With the tissue T between the anvil head 41 and the shell assembly 20, the anvil shaft 42 is positioned within the shell assembly 20.

With reference to FIGS. 13 and 14, with the trocar 110 coupled to the anvil shaft 42 of the anvil assembly 40, the trocar 110 is drawn proximally to approximate the anvil head 41 towards the staple cartridge 12 of the shell assembly 20 such that the tissue T is clamped between the anvil head 41 and the staple cartridge 12. As the tissue T is clamped between the anvil head 41 and the staple cartridge 12, a retraction force required to proximally draw the trocar 110 is increased as the tissue T is compressed between the anvil head 41 and the staple cartridge 12. As the retraction force increases, the distal wall 116 defining the notch 114 of the trocar 110 urges the retaining ring 49 of the expandable collar 47 of the anvil shaft 42 radially outward into engagement, or further engagement with, the proximal portion 36 of the bushing 30 such that the outer surface 47a of the resilient legs 44a defining the expandable collar 47 engages distal portion 31a the inner surface 31 of the bushing 30 to retain the retaining ring 49 within the notch 114 of the trocar 110. As the retraction force increases, the expansion force increases. In addition, as the expansion force increases, the friction between the outer surface 47a and the inner surface 31 increases requiring additional retraction force to approximate the anvil head 41. It is contemplated that the distal portion 31a of the inner surface 31, the proximal portion 31b of the inner surface 31, and/or the outer surface 47a of the expandable collar 47 may be configured to reduce friction. For example the surfaces 31a, 31b, 47a may be smooth, constructed with a slippery material, and/or coated with a lubricant.

With reference to FIGS. 15 and 16, when the outer surface 47a of the expandable collar 47 engages the proximal portion 31b of the inner surface 31 of the bushing 30 proximal to the expandable section 38, the retraction force deforms the expandable section 38 from the initial configuration to the stretched configuration. It is contemplated that the proximal portion 31b may be configured to increase friction with the outer surface 47b. The deformation of the expandable section 38 reduces the retraction force required to complete approximation of the anvil head 41 with the staple cartridge 12 of the shell assembly 20 by eliminating the need to overcome the friction caused by the sliding of the outer surface 47a against the inner surface 31.

Figure 17:
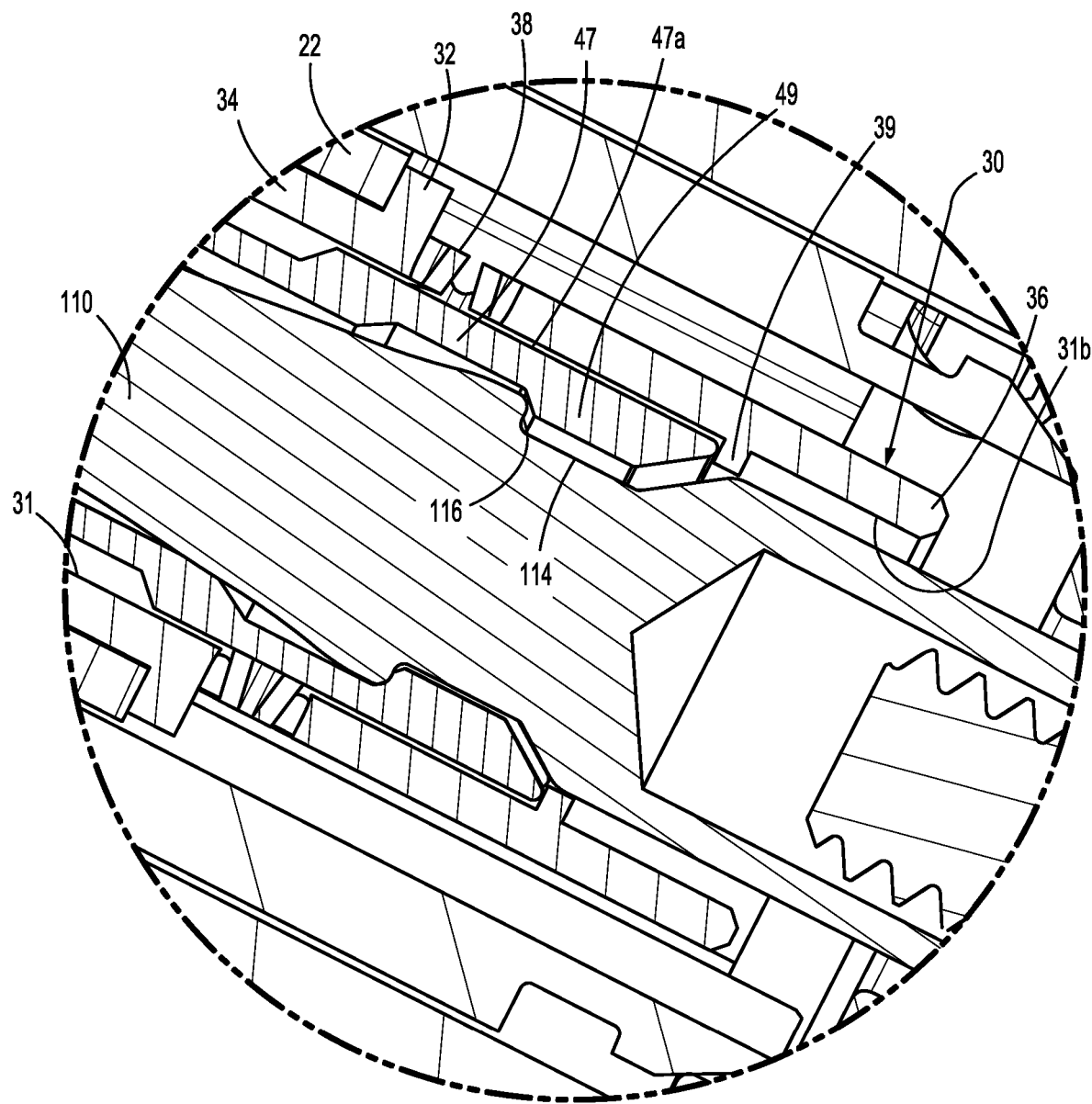
FIG. 17 is an enlarged cross-sectional view of a portion of another bushing in accordance with the present disclosure including an engagement flange engaged by the anvil shaft.

Referring to FIG. 17, the proximal portion 36 of the bushing 30 may include an engagement flange 39 extending inward from the inner surface 31. The engagement flange 39 is engaged by the anvil shaft 42 as the anvil head 41 is substantially approximated with the staple cartridge 12 the shell assembly 20. When the anvil shaft 42 engages the engagement flange 39, additional retraction of the anvil shaft 42 in response to retraction of the trocar 110 deforms the expandable section 38 without requiring the outer surface 47a of the expandable collar 47 to engage the inner surface 31 of the bushing 30. By not requiring the outer surface 47a to engage the inner surface 31, the retraction force to complete approximation of the anvil head 41 may be further reduced. In addition, the retraction force required for full approximation of the anvil head 41 with the staple cartridge 12 may be more easily calibrated to a clamping force applied by the anvil head 41 to tissue T between the anvil head 41 and the staple cartridge 12 of the shell assembly 20.

It is noted that the anvil retainer is described as including a trocar and the anvil shaft is described as including a plurality of resilient legs that receive the trocar; however, these components may be reversed, i.e., the anvil shaft can define a trocar and the anvil retainer can include resilient legs that receive the trocar of the anvil shaft.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. The present disclosure is not limited to circular stapling loading units, but has application to loading units for linear stapling or other types of instruments, such as electrocautery or ultrasonic instruments. Therefore, the above description should not be construed as limiting, but merely as exemplifications of particular embodiments.

Those skilled in the art will envision other modifications within the scope of the claims appended hereto.

What is claimed:

1. A shell assembly comprising:
   a housing defining a longitudinal axis and a cavity and including an inner cylinder positioned within the cavity;
   a cartridge supported on the housing including a plurality of staples; and
   a hollow bushing secured to the inner cylinder and positioned within the cavity, the hollow bushing including:
   a distal portion and a proximal portion formed of a rigid material, wherein a portion of the hollow bushing is longitudinally fixed to the housing; and
   an expandable portion connecting the distal and proximal portions, the hollow bushing having an initial configuration defining a first length along the longitudinal axis and a stretched configuration defining a second length along the longitudinal axis greater than the first length.

2. The shell assembly according to claim 1, wherein the expandable portion includes a plurality of legs that are bent in the initial configuration and straightened in the stretched configuration.

3. The shell assembly according to claim 2, wherein in the stretched configuration each leg of the plurality of legs are aligned with the longitudinal axis.

4. The shell assembly according to claim 1, wherein the expandable portion defines a helical slot that passes through the expandable portion, the helical slot compressed in the initial configuration and expanded in the stretched configuration.

5. The shell assembly according to claim 1, wherein the hollow bushing includes a central flange positioned between the distal portion and the expandable portion, the central flange sized to prevent the hollow bushing moving distally through the inner cylinder.

6. The shell assembly according to claim 1, wherein a distal portion of the hollow bushing has engagement features that longitudinally fix the hollow bushing within the housing, the engagement features including annular ribs, the annular ribs engaging the inner cylinder.

7. A surgical instrument comprising:
   an anvil retainer having a distal end portion and a proximal end portion,
   an anvil assembly having an anvil head and an anvil shaft extending proximally from the anvil head, the anvil shaft having resilient legs secured about the anvil retainer; and
   a shell assembly including:
   a housing defining a longitudinal axis and a cavity;
   a cartridge supported on the housing including a plurality of staples; and
   a hollow bushing positioned within the cavity and configured to prevent the anvil shaft from being disengaged from the anvil retainer, the hollow bushing including a distal portion and a proximal portion formed of a rigid material, wherein a portion of the hollow bushing is longitudinally fixed to the housing and an expandable portion connects the distal and proximal portions, the hollow bushing having an initial configuration defining a first length along the longitudinal axis and a stretched configuration defining a second length along the longitudinal axis greater than the first length.

8. The surgical instrument according to claim 7, wherein the proximal end portion of the anvil retainer defines a notch, and wherein the resilient legs of the anvil shaft include a retaining ring extending inward from an inner surface thereof, the retaining ring positionable within the notch of the anvil retainer to secure the anvil shaft to the anvil retainer.

9. The surgical instrument according to claim 8, wherein the resilient legs of the anvil shaft define an expandable collar, the expandable collar radially expanding in response to retraction of the anvil retainer, the hollow bushing preventing the retaining ring from disengaging the notch of the anvil retainer when the resilient legs of the anvil shaft are disposed within the hollow bushing.

10. The surgical instrument according to claim 9, wherein retraction of the anvil retainer approximates the anvil head towards the shell assembly.

11. The surgical instrument according to claim 7, wherein the resilient legs of the anvil shaft engages the proximal portion of the hollow bushing to expand the hollow bushing from the initial configuration towards the stretched configuration in response to retraction of the anvil retainer.

12. The surgical instrument according to claim 7, wherein the distal end portion of the anvil retainer is tapered and the resilient legs of the anvil shaft radially expand as the anvil shaft receives the tapered distal end portion of the anvil retainer.

13. The surgical instrument according to claim 12, wherein the anvil retainer is extendable distally such that a notch defined by the anvil retainer is positionable beyond the hollow bushing to couple the anvil retainer to the anvil shaft.

14. The surgical instrument according to claim 9, wherein the proximal portion of the hollow bushing includes an engagement flange extending inward from an inner surface thereof, the expandable collar configured to engage the engagement flange.

15. The surgical instrument according to claim 14, wherein engagement of the expandable collar with the engagement flange expands the hollow bushing from the initial configuration towards the stretched configuration in response to retraction of the anvil retainer.

16. The surgical instrument according to claim 15, wherein the expandable collar is configured to radially expand such that an outer surface of the expandable collar engages an inner surface of the hollow bushing.

17. The surgical instrument according to claim 16, wherein the outer surface of the expandable collar frictionally engages the inner surface of the hollow bushing to expand the hollow bushing from the initial configuration towards the stretched configuration.

* * * * *